United States Patent [19]
McCamy et al.

[11] Patent Number: 5,587,221
[45] Date of Patent: Dec. 24, 1996

[54] INSECTICIDAL CARPET AND PRETREATMENT PROCESS FOR PRODUCING INSECTICIDAL CARPET

[76] Inventors: T. H. McCamy, P.O. Box 962, Dalton, Ga. 30722; William H. H. Clark, P.O. Box 8, Ringgold, Ga. 30736

[21] Appl. No.: 359,401

[22] Filed: Dec. 20, 1994

[51] Int. Cl.⁶ .......................... B23B 3/02; A01N 25/34; A01N 59/14; A01N 33/22; A61K 33/22
[52] U.S. Cl. .......................... 428/96; 424/411; 424/657; 424/658; 424/659; 424/660; 514/875
[58] Field of Search .......................... 428/96; 424/411, 424/657, 658, 659, 660; 514/875

[56] References Cited

U.S. PATENT DOCUMENTS

| | | | |
|---|---|---|---|
| 3,317,372 | 5/1967 | Hart | 429/96 |
| 4,363,798 | 12/1982 | D'Orazio | 424/84 |
| 4,374,853 | 2/1983 | Workman | 424/303 |
| 4,438,090 | 3/1984 | Brite | 424/7.1 |
| 4,439,488 | 3/1984 | Trimmell et al. | 428/402.24 |
| 4,461,758 | 7/1984 | Brite | 424/10 |
| 4,610,881 | 9/1986 | Bechgaard | 424/148 |
| 4,617,188 | 10/1986 | Page et al. | 424/148 |
| 4,636,343 | 1/1987 | Shibanai | 264/118 |
| 4,657,582 | 4/1987 | Huber | 71/121 |
| 4,759,930 | 7/1988 | Granirer et al. | 424/148 |
| 4,765,982 | 8/1988 | Romming et al. | 424/403 |
| 4,804,683 | 2/1989 | Steltenkamp | 514/629 |
| 4,826,682 | 5/1989 | Sakharova | 424/623 |
| 4,873,084 | 10/1989 | Sallay | 424/658 |
| 4,906,488 | 3/1990 | Pera | 426/573 |
| 4,958,456 | 9/1990 | Chaudoin et al. | 43/124 |
| 4,961,930 | 10/1990 | Perdelwitz, Jr. et al. | 424/411 |
| 5,079,063 | 1/1992 | Plischke et al. | 428/95 |
| 5,127,367 | 7/1992 | Starowitz, Jr. | 119/28.5 |
| 5,151,127 | 9/1992 | Thompson | 106/15.05 |
| 5,314,699 | 5/1994 | Baden | 424/660 |

*Primary Examiner*—Terrel Morris
*Attorney, Agent, or Firm*—Deveau. Colton & Marquis

[57] ABSTRACT

A process for pretreating a carpet to give the carpet insecticidal, fungicidal and bacteriacidal properties, and the resulting carpet product. The process is incorporated into the carpet manufacturing process to eliminate the necessity of treating carpets subsequent to the manufacturing process. A portion of the carpet is saturated with a mixture comprising boric acid and a boron-containing salt dissolved in an aqueous solvent. A heat drying step is then used to drive off the aqueous solvent after which a portion of the boron-containing salt remains on the backing. The preferred mixture contains a combination of boric acid and borax in an aqueous solution. The ratio of boric acid to borax ranges from 0.5:1 to 3:1, and the percent strength of the borax/boric acid combination in the solution is preferably from 0.1% to 3.125%.

20 Claims, No Drawings

INSECTICIDAL CARPET AND PRETREATMENT PROCESS FOR PRODUCING INSECTICIDAL CARPET

BACKGROUND OF THE INVENTION

1. Field of the Invention

The present invention relates generally to a process for pretreating a carpet with an insecticide during the carpet manufacturing and/or dyeing process and, more particularly, to a carpet pretreatment process which is incorporated into the carpet manufacturing and/or dyeing process to produce a carpet which is capable of controlling insects through action upon the insect larvae.

2. Prior Art

Approximately half of the households in America have a pet, usually either a dog or cat. Most of these animals, at some point, will become infested with fleas, usually the cat flea, *Ctenocephalides felis*, and/or the dog flea, *Ctenocephalides canis*. Fleas consume the animal's blood and cause irritation at the site of the bite, but their most devastating effect is on the immune system. When a flea bites, it injects a small amount of protein to keep blood from coagulating as it draws blood up through its proboscis. The host animal often develops an allergy to this foreign protein. The immune system reacts to cause an extreme and continuous itching sensation at the site of the bite.

The diagnostic signs exhibited by an animal with flea allergy are the result of the animal's reaction to this itching. They may lick and bite at the site of the flea bite until they remove the hair and denude the skin, leaving an area that is raw and bleeding. Over a period of weeks, the entire rear half of the animal may be denuded of hair, leaving the skin raw in some places and thickened in others. The animal may be in constant discomfort, and may develop an aggressive change in personality. Thus far, there are no cures for allergic conditions. Relief from the itching usually involves treatment with anti-inflammatory drugs available only from a licensed veterinarian. Over a period of time, these drugs can cause undesirable side effects to the health of the animal.

Fleas brought into the house by pets also may be detrimental to the health of the family of the owner. These fleas prefer to feed on dogs or cats but will feed on the owner if the pet is not readily available. They not only become an irritant, but are the intermediate host of a dog tapeworm that also can infect the family of the owner.

Floor carpets provide an excellent environment for the propagation of fleas. The temperature and humidity within the home is ideal, the pet provides a food supply, and the fibers of the carpet provide the protection from both physical damage and sunlight. Once a flea population is established in the carpet, it is very difficult to eliminate. Efforts may include sprays, dust, aerosol bombs containing insecticides, growth inhibitors and the shampooing of the carpet. These efforts may help but often they are expensive, troublesome, odorific and seldom entirely successful. Even when some degree of control is obtained, the animals go outside, gather up a new crop of fleas, bring them into the home and the cycle starts all over again.

Consequently, flea control in the home has become a billion dollar a year business. Drug stores, supermarkets, and pet stores carry many flea control products. The reason there are so many is that none of them work well on carpet. The carpet not only is an excellent environment for growing fleas, but the carpet fibers also tend to protect the flea from insecticides by either covering the insect or soaking up so much of the insecticide that the flea survives. Shampooing the carpet only is marginally effective even if all furniture is removed and every carpet in the house is shampooed.

Like all insects, the flea has a four stage life cycle. Female fleas on the animal lay eggs, stage one, which fall to the carpeted floor and hatch into larvae, stage two. These larvae are very sensitive to light and make their way as deeply into the carpet as possible. In about two weeks the larvae spin cocoons, stage three, and in another two weeks they are ready to hatch into adults, stage four, anytime a potential blood meal comes within striking distance. The life cycle is accelerated by increased heat and humidity or slowed with coolness and dry air. The egg and cocoon, or pupa, are well protected by their covering shell and very resistant to environmental changes or control methods. The adult flea is susceptible to insecticides but the other stages living in the carpet usually develop faster than control methods can eliminate the adults from the animal. The larvae seems to be the most susceptible stage around which to develop a successful flea control program.

Carpets also may harbor pests that are of even greater public health significance than fleas. Almost twenty percent of the American population suffer from allergies. Many of these allergies have a bacterial, fungal, or dust mite component that may be growing in the home carpet.

It is generally known in the insecticide industry that certain boron-containing compounds can be used as insecticides. Borates have the unique characteristic of being cellular toxins to insects, such as flea larvae, yet remaining relatively non-toxic to humans and other mammalian species. The scientific literature also indicates that borates have potential in helping to control bacteria, fungus, and mites. The following patents generally illustrate the use of boron-containing compounds as insecticides.

Baden, U.S. Pat. No. 5,314,699, discloses a post-installation combination insecticidal and carpet cleaning treatment which consists of adding four to eight ounces of disodium octaborate tetrahydrate to each gallon of cleaning solution (approximately 3.125%–6.25% solution). The combination is applied to a carpet through a common carpet shampooing device for providing flea control. D'Orazio, U.S. Pat. No. 4,363,798, teaches an outdoor termite control compound which utilizes boron compounds selected from colemanite, ulexite and calcium boride in mixtures sufficient to kill termites without creating bait shyness. Bechgaard, U.S. Pat. No. 4,610,881, discloses a wood treatment compound which consists of mixing a boron-rich compound in a liquid carrier and applying the mixture to a porous substrate, such as timber, to protect it from attack from insects or fungi. Page, et al., U.S. Pat. No. 4,617,188, discloses the use of borax to kill insects, such as cockroaches. Granirer, et al., U.S. Pat. No. 4,759,930, discloses an insecticide using compositions comprised of various mixtures of eucalyptus, rosemary, peppermint and boric acid with pyrethrum, rotenone, or both, to kill insects, such as cockroaches.

Although the use of certain boron-containing compounds to kill insects and certain types of fungi is generally known, the present invention proposes using a unique combination of boric acid and disodium tetraborate decahydrate (borax) in an aqueous solvent which, before the present invention, apparently was not known to be useful for killing insects, and controlling the growth of bacteria and fungi. The composition is applied to the carpet during the carpet manufacturing process. The composition can be applied to the carpet backing or to the backing and fibers of the carpet, and can be applied during the dyeing or final treatment processes. The composition operates as an insecticide to kill flea larvae which end up in the carpet. Moreover, the process of the present invention is a pretreatment process wherein the carpet backing is treated during the carpet manufacturing process. The prior art does not teach or suggest such a pretreatment process.

The general idea of injecting an insecticide into a substrate or into fibers is known. For example, Plischke, et al., U.S. Pat. No. 5,079,063, teaches incorporating an antiflea agent, such as d-limonen, which is a terpine, into filaments which are processed into yarn for making textile fabrics and carpets. Pera, U.S. Pat. No. 4,906,488, discloses the incorporation of agents into synthetic fibers and the release of the agents from within the fibers as the agent on the surface of the fibers dissipates. Ronning, et al., U.S. Pat. No. 4,765,982, discloses self-adhering an insect control agent to a rough-surfaced fiber which may be incorporated into webs, sheets, mats, and fabrics. Perdelwitz, Jr., et al., U.S. Pat. No. 4,961,930, discloses producing a pet pad by incorporating an insecticide into a mixture of thermoplastic and other fibers prior to thermobonding so that the insecticide is fixed in the pad during thermobonding. Starowitz, Jr., U.S. Pat. No. 5,127,367, discloses an animal mat comprised of a top and a bottom layer of biodegradable paper and an intermediate layer of cellulose material. Small packages of insect killing powder can be incorporated into the construction of the mat for killing insects.

Therefore, it can be seen from the foregoing discussion that it is generally known to incorporate an insecticide into raw fibers and other materials. As stated above, it is also generally known to use boron compounds to kill insects. However, the present invention utilizes a mixture of borax and boric acid in an aqueous solution wherein up to 3.125% of the solution represents the boric acid/borax combination. None of the prior art teaches or suggests the use of such a mixture as an insecticide for pretreating carpets prior to distribution. Unlike prior processes, the insecticide of the present invention is applied during a pretreatment process which occurs during the manufacturing of the carpet.

SUMMARY OF THE INVENTION

In accordance with the present invention, a solution of boric acid and disodium tetraborate decahydrate (borax) are combined in an aqueous medium to form an insecticidal and/or larvacidal solution, which is used during the carpet manufacturing process as an insecticide to treat carpet backings and carpet fibers. The preferred ratio of boric acid to borax is approximately 0.5:1 to 3:1 and, when combined in the aqueous medium, the boric acid and borax together represent approximately 0.1 to 3.125% of the solution. The strength of the solution may vary, depending both upon several factors, including the weight of the carpet. A relatively low percentage of boric acid/borax is needed, which is advantageous because, although borates are relatively non-toxic to humans, the current environmental regulatory atmosphere dictates that as little as necessary of the borate combination should be used.

In accordance with the preferred embodiment of the present invention, during the manufacturing process the carpet backing is saturated with a solution comprising a boron-containing salt dissolved in an aqueous solvent. The aqueous solvent is then driven off in such a manner that a portion of the boron-containing salt contained in the solution remains on the backing. The carpet fibers are then attached to the backing. In an alternative embodiment, both the carpet backing and the carpet fibers can be saturated with the solution during the manufacturing process, and, in particular, during the dyeing process. Once the aqueous solvent is driven off, a portion of the boron-containing salt contained in the solution remains on the backing and fibers. The solution comprising a boron-containing salt also can be contained in the wash-box, applied in a fashion similar to softeners, or applied with a separate applicator. Each embodiment constitutes a pre-consumer treatment process used to produce a carpet for controlling insects, such as fleas, and certain types of bacteria and fungus.

Accordingly, it is an object of the present invention to provide a process for treating carpets during manufacture with an insecticide to control flea larvae.

It is also an object of the present invention to provide a process for treating carpets with an insecticide which can be incorporated into the carpet manufacturing process.

It is another object of the present invention to provide an insecticide for treating carpets to control flea larvae which is inorganic and relatively non-toxic.

It is yet another object of the present invention to provide an insecticide for treating carpets which is relatively inexpensive to produce.

It is yet another object of the present invention to provide a process for treating carpets to control flea larvae which is cost effective.

It is yet another object of the present invention to provide a carpet for controlling insects, bacteria and fungi.

These objects and other objects, features and advantages of the present invention will become apparent from the following detailed description and claims.

DETAILED DESCRIPTION OF THE INVENTION

The invention comprises both a carpet pretreatment process which renders insecticidal properties to a carpet, and the resultant insecticidal carpet produced from the process. The carpet treatment process of the present invention preferably is incorporated into the carpet manufacturing process. During the normal carpet manufacturing process, carpet fibers are tufted into a cloth or plastic backing. These fibers may be dyed either before or after the manufacturing process. If fibers are used which have been dyed prior to the manufacturing process, the carpet backing first is treated with the solution of the present invention. Once the layer of inorganic non-toxic insecticide has been applied to the carpet backing, the pre-dyed fibers are tufted into the carpet backing.

Alternatively, both the carpet backing and the fibers can be treated with the insecticide. The carpet fibers are tufted into the carpet backing, dyed, rinsed, and heat dried in a continuous process on rolls up to 12 feet wide. The solution of the present invention preferably is applied after the excess dye has been rinsed, but before the heat drying process. The solution can be applied by dip, spray, or saturated roller, which are conventional techniques used in the industry. During the heat drying process, the water is driven off leaving the inorganic non-toxic insecticide of the present invention coating the backing and the fibers. The final product is a treated carpet having excellent insecticidal, bacteriacidal and fungicidal properties.

During the normal carpet manufacturing process, carpet fibers are tufted into a cloth or plastic backing. These fibers may be color dyed either before or after the manufacturing process. Where pre-dyed fibers are tufted into a backing, the backing can be coated with the solution of the present invention before the tufting process. This is the preferred method of treatment, as flea larvae tend to migrate downward, away from light, and generally end up in the carpet backing. By applying the solution of the present invention only to the carpet backing, and not to the fibers, less of the solution is necessary, resulting in a more economical process. Current methods tend to treat the entire carpet, especially post-manufacture, post-installation treatments.

Alternatively, if un-dyed fibers are used, the fibers are usually tufted into the carpet backing and the carpet, including the fibers, is dyed, rinsed and heat dried in a continuous process on rolls up to twelve feet wide. The solution of the present invention can be applied to the carpet after the dye has been rinsed but before the heat drying process. The water is driven off during the heat drying process leaving the inorganic non-toxic insecticide coating the backing and fibers. Such a process is neither disclosed nor suggested in the prior art.

Overall, the primary advantage of the present invention is that, by treating the carpet backing, control of flea larvae is increased. As discussed above, flea larvae are sensitive to light and move to the bottom of carpeting as quickly as possible. In accordance with the present invention, a layer of inorganic non-toxic insecticide is available when the larvae reach the bottom of the carpet.

Another advantage is that the insecticide solution of the present invention is cheaper to make than most of the insecticides now used to treat carpets, including many of those mentioned previously, which results in a less expensive treatment process. For example, octaborates have been used in the industry as insecticides to treat carpets. The present invention utilizes a tetraborate plus boric acid in an aqueous solution which works as well as octaborate but costs less because obtaining octaborate requires the additional step and expense of driving off a certain amount of water. The treatment process of the present invention may cost pennies per yard compared to dollars per yard required by other known treatment processes. Therefore, the present invention proposes a less expensive carpet treatment process which can be incorporated into the carpet manufacturing process thereby saving costs while eliminating the need to treat the carpet after it has been manufactured.

Yet another advantage is that the insecticide is applied to the carpet as a pretreatment process prior to the carpet being sold and distributed to the consumer. As a result, the consumer purchases a product already containing an insecticide which, when installed, immediately begins to help control any flea population present in the house.

The solution of the present invention preferably consists of a combination of boric acid and borax in an aqueous solution. The percentage of the boric acid/borax combination in the aqueous solution is preferably approximately 3.0% but may range from 0.1% up to 3.125%. The preferred range of boric acid/borax is from approximately 1.5% to approximately 3.0%. The weight ratio of boric acid to borax ranges from approximately 0.5:1 to 3:1. It has been found that the best insecticidal results relative to cost occur when up to 1½ ounces of the boric acid/borax combination is applied to each square yard of carpet. Preferably, approximately ½ to 1 ounce of the boric acid/borax combination is applied to each square yard of carpet.

A number of different borate compounds may be suitable for use with the process of the present invention. These compounds include boric oxide, metabolic acid, disodium tetraborate pentahydrate, disodium tetraborate tetrahydrate, disodium tetraborate decahydrate, disodium tetraborate (anhydrous borax), disodium octaborate tetrahydrate, disodium octraborate trihydrate, disodium pentaborate, ammonium borates, and the potassium borates.

One of the easiest methods for applying the boric acid/borax to the carpet without interfering with the carpet manufacturing process, without retrofitting the carpet manufacturing line, and without possibly releasing the boric acid/borax from the carpet during subsequent manufacturing or treatment stages, is to apply the boric acid/borax to the carpet in a final wash box. After the carpet has been manufactured and dyed, the carpet typically is washed and, possibly, treated with softeners and/or stain resisting compounds. The boric acid/borax may be applied to the carpet at this stage using an existing wash box or treatment box at the end of the carpet production line.

TESTING

A study was performed to determine if a combination of boric acid/borax is an effective larvacide against the larvae of *Ctenocephalides felis*. The tests were conducted with 3.125% and 1.5625% strength boric acid/borax in an aqueous solution. The following is a discussion of these tests and their results.

A sample of nylon carpet was cut into three eighteen-inch squares. The first square was maintained as an untreated control, the second square was saturated with a 3.125% solution of 1:1 boric acid/borax, and the third square was saturated with a 1.5625% solution of 1:1 boric acid/borax. Treated samples were hung on a line to drain and dry. When dry, a metal circle was used to cut circles of carpeting two inches in diameter. Each circle was placed in a plastic cup with a bottom inside diameter of two inches. The bottom of the cups were slightly convex so approximately ¼ inch of building sand was placed in the bottom of each cup before placing the carpet samples in the cups. Fifty eggs of *Ctenocephalides felis* were counted into each cup. A small amount of dried bovine blood was sprinkled onto each piece of carpet in the cups. Cups were incubated at 80° F. (+/−5° F.) at 80% relative humidity (+/−5%).

Larvae were harvested from one cup each of the control, 3.125% and 1.5625% treated carpet samples at the end of 1, 2, 3 and 5 days. The number of larvae are charted in Table 1.

TABLE I

| | Number of C felis Larvae Harvested | | |
|---|---|---|---|
| Day | Control | 1.5625% Solution | 3.125% Solution |
| 1 | 27 | 7 | 8 |
| 2 | 38 | 1 | 1 |
| 5 | 35 | 0 | 0 |

In the tests, an average of 35 larvae were harvested from each inoculation of 50 eggs per cup. This recovery rate of 70% would seem to be a function of the normal hatching rate plus the trauma of shipment and manipulation.

Fewer live larvae were harvested from the control on the first day than on the following days. It is likely that all the eggs were not yet hatched. Eggs were one to five days in age when they were inoculated into the cups. On the first day, a number of live larvae were recovered from the treated samples. It is likely that they had not yet succumbed to the effects of the larvacide.

After the second day, the larvae in the control samples had consumed enough of the dried blood so that they turned dark and could be more easily identified on a white background rather than the dark background of the glass. They were also larger and became more active as they matured.

On the third day, 13 live larvae were found in the sample treated with the 6.25% solution. All but one of these were found in the sand under the pad. They were still clear in color and small. This would seem to indicated that the pad must have been tilted, thus allowing the larvae to freely enter the sand and miss both the blood meal and the larvacide.

Approximately 104 live larvae, harvested from the controls, were placed in one cup treated with the 3.125% solution, as they were harvested on days 1, 2, and 3. At the end of day 5 the pad in this cup was examined. No live larvae were found on the pad but 15 were found in the sand underneath.

The conclusion of the tests was that a 1:1 solution of boric acid is equally effective against fleas and flea larvae in household carpeting at both 3.125% strength and 1.5625% strength. As most common insecticides use a higher percentage of the borate compounds, it was surprising that a 1.5625% solution appeared to be equally effective. Using a 1.5625% or less solution is more economical and introduces less of the insecticide to the home environment. The combination of roughly equivalent efficacy at a lower strength and the process of pretreating the carpet prior to sale to the consumer, results in a novel, economical carpet treatment process and carpet product.

Four pieces of carpet were cut, each 18 inches in diameter. One piece was treated with 3% boric acid, one with 3% borax, one with a 3% combination of 1:1 boric acid:borax, and one was left untreated as a control. Pieces were inoculated with bacteria and fungus.

Two square inches from each piece of carpet were cut antiseptically and placed in separate sterile glass jars. Thirty 30cc of sterile distilled water was added to each jar and the jars agitated. Thirty drops of fluid then were taken from each jar and placed on separate EMB plates for bacteria growth. For fungal growth, petri dishes of Saboroid's media were marked into quarters. Five drops of fluid were taken from each jar and spread throughout the 1st quarter. A loop was then flamed and one streak taken across quarter 1 into quarter 2 and then spread throughout quarter 2. This was repeated for quarters 2 through 4. Plates were incubated at 75° F. for three days. One of each type of petri dish was also inoculated with sterile water as an additional control.

Fungal Results

About six fungal colonies were found in the water control dishes indicating a minor degree of contamination.

Growth covered quarters 1 and 2 in the control dishes, but thinned out in quarters 3 and 4, suggesting a good degree of inoculation.

Growth in the boric acid plates had almost as much growth as in the untreated control plates, indicating that boric acid alone had very little effect in controlling the growth of fungus.

The borax plates had approximately 25% as much growth as the untreated control plates, indicating that borax alone has a relatively good degree of effect in controlling the growth of fungus.

The boric acid/borax plate had less than 10 isolated colonies of growth, indicating an excellent degree of control of the growth of fungus.

Bacterial Results

Two colonies were found in the water control indicating some degree of contamination.

A good sheet of growth covered the entire petri dish of the untreated control dish indicating a good degree of inoculation.

A thin sheet of growth also covered the bottom of the borax dish but only at approximately 80% of the growth amount found in the control dish.

No colonies were found in the boric acid dish indicating a good degree of control.

No colonies were found in the boric acid/borax dish, indicating a good degree of control. Overall, a combination of boric acid and borax is excellent at controlling the growth of fungi and bacteria.

The present invention has been described with respect to particular embodiments. It will be apparent to those skilled in the art that many variations to these embodiments exist which are within the spirit and scope of the present invention.

We claim:

1. A carpet possessing insecticidal, bactericidal and fungicidal properties, said carpet comprising a carpet backing and carpet fibers, wherein the carpet has been treated with a solution comprising:
   (a) a mixture consisting of boric acid and disodium tetraborate decahydrate; and
   (b) an aqueous medium.

2. The carpet of claim 1, wherein the concentration of said mixture in the solution comprising said mixture and said aqueous medium is from 0.1% to 3.0% and wherein the carpet has been treated with enough of the solution to deposit up to 1.5 ounces of said mixture per square yard of carpet.

3. The carpet of claim 2, wherein the concentration of said mixture in the solution comprising said mixture and said aqueous medium is from 0.1% to 3.0% and wherein the carpet has been treated with enough of the solution to deposit 0.5 to 1.5 ounces of said mixture per square yard of carpet.

4. The carpet of claim 3, wherein the concentration of said mixture in the solution comprising said mixture and said aqueous medium is from 1.5% to 3.0% and wherein the carpet has been treated with enough of the solution to deposit 0.5 to 1.5 ounces of said mixture per square yard of carpet.

5. The carpet of claim 1, wherein the ratio of boric acid to disodium tetraborate decahydrate in said mixture is from 0.5:1 to 3:1.

6. The carpet of claim 2, wherein the ratio of boric acid to disodium tetraborate decahydrate in said mixture is from 0.5:1 to 3:1.

7. The carpet of claim 3, wherein the ratio of boric acid to disodium tetraborate decahydrate in said mixture is from 0.5:1 to 3:1.

8. The carpet of claim 4, wherein the ratio of boric acid to disodium tetraborate decahydrate in said mixture is from 0.5:1 to 3:1.

9. The carpet of claim 1, wherein said aqueous medium consists of water.

10. A carpet possessing insecticidal, bactericidal and fungicidal properties, said carpet consisting essentially of a carpet backing and carpet fibers, wherein said carpet has been treated with a solution consisting essentially of:
   (a) a mixture consisting of boric acid and disodium tetraborate decahydrate; and (b) an aqueous medium.

11. The carpet of claim 10, wherein the concentration of said mixture in the solution consisting essentially of said mixture and said aqueous medium is from 0.1% to 3.0% and wherein the carpet has been treated with enough of the solution to deposit up to 1.5 ounces of said mixture per square yard of carpet.

12. The carpet of claim 11, wherein the concentration of said mixture in the solution consisting essentially of said mixture and said aqueous medium is from 0.1% to 3.0% and wherein the carpet has been treated with enough of the solution to deposit 0.5 to 1.5 ounces of said mixture per square yard of carpet.

13. The carpet of claim 12, wherein the concentration of said mixture in the solution consisting essentially of said mixture and said aqueous medium is from 1.5% to 3.0% and the carpet has been treated with enough of the solution to deposit 0.5 to 1.5 ounces of said mixture per square yard of carpet.

14. The carpet of claim 10, wherein the ratio of boric acid to disodium tetraborate decahydrate in said mixture is from 0.5:1 to 3:1.

15. The carpet of claim 11, wherein the ratio of boric acid to disodium tetraborate decahydrate in said mixture is from 0.5:1 to 3:1.

16. The carpet of claim 12, wherein the ratio of boric acid to disodium tetraborate decahydrate in said mixture is from 0.5:1 to 3:1.

17. The carpet of claim 13, wherein the ratio of boric acid to disodium tetraborate decahydrate in said mixture is from 0.5:1 to 3:1.

18. The carpet of claim 10, wherein said aqueous medium consists of water.

19. A carpet possessing insecticidal, bactericidal and fungicidal properties, said carpet comprising a carpet backing and carpet fibers, wherein only the carpet backing is treated with a solution comprising:

(a) a mixture consisting of boric acid and disodium tetraborate decahydrate; and (b) an aqueous medium.

20. The carpet of claim 19, wherein the concentration of said mixture in the solution comprising said mixture and said aqueous medium is from 0.1% to 3.0%, wherein the ratio of boric acid to disodium tetraborate decahydrate in said mixture is from 0.5:1 to 3:1, wherein the aqueous medium is water, and wherein the carpet is treated with enough of the solution to deposit from 0.5 to 1.5 ounces of said mixture per square yard of carpet.

* * * * *